(12) United States Patent
Jeon et al.

(10) Patent No.: US 10,231,844 B2
(45) Date of Patent: Mar. 19, 2019

(54) CAGE ASSEMBLY FOR SPINE INTERBODY FUSION

(71) Applicant: DIOMEDICAL CO., LTD., Seongnam-si (KR)

(72) Inventors: Chang-hoon Jeon, Seoul (KR); Jong-woo Kim, Seongnam-si (KR); Jin-tae Moon, Hanam-si (KR); Ye-sol Lee, Seoul (KR); Gi-yeon Won, Seongnam-si (KR); Il-Jin Jeon, Seoul (KR)

( * ) Notice: Subject to any disclaimer, the term of this patent is extended or adjusted under 35 U.S.C. 154(b) by 39 days.

(21) Appl. No.: 14/905,936

(22) PCT Filed: Mar. 9, 2015

(86) PCT No.: PCT/KR2015/002257
§ 371 (c)(1),
(2) Date: Jan. 18, 2016

(87) PCT Pub. No.: WO2015/137675
PCT Pub. Date: Sep. 17, 2015

(65) Prior Publication Data
US 2016/0367378 A1 Dec. 22, 2016

(30) Foreign Application Priority Data
Mar. 12, 2014 (KR) .......................... 10-2014-0028919

(51) Int. Cl.
*A61F 2/44* (2006.01)
*A61F 2/30* (2006.01)

(52) U.S. Cl.
CPC ............ *A61F 2/447* (2013.01); *A61F 2/4465* (2013.01); *A61F 2002/30736* (2013.01);
(Continued)

(58) Field of Classification Search
CPC ............ A61F 2/4455–2/447; A61F 2002/4475
See application file for complete search history.

(56) References Cited

U.S. PATENT DOCUMENTS

2003/0069640 A1\* 4/2003 Ferreira .................... A61F 2/28
623/17.11
2003/0114931 A1\* 6/2003 Lee ........................ A61F 2/4455
623/17.11
(Continued)

FOREIGN PATENT DOCUMENTS

JP 2012-019919 2/2012
KR 10-2008-0113029 12/2008
(Continued)

OTHER PUBLICATIONS

English translation of 10-1992-0701023.
(Continued)

*Primary Examiner* — Matthew J Lawson
*Assistant Examiner* — Amy R Sipp
(74) *Attorney, Agent, or Firm* — Antonio Ha & U.S. Patent, LLC

(57) ABSTRACT

The present invention relates to a cage assembly for spinal interbody fusion comprising: a main body which is inserted between a vertebral body of a spine from which a disc is removed, and a neighboring vertebral body; a first screw part which is formed on the upper surface of the main body, and which has a spiral shape formed along a first direction heading outward from the center; a second screw part which is formed on the lower surface of the main body, and which has a spiral shape formed along a second direction heading outward from the center; and a space part which is formed to penetrate the upper surface and the lower surface of the main body, and which enables the bones forming the vertebral body and the neighboring vertebral body to fuse together. The purpose of the present invention is to promote
(Continued)

the smooth progress of surgery for the bone fusion of two neighboring vertebral bodies, or more than two vertebral bodies, forming the spine.

17 Claims, 4 Drawing Sheets

(52) U.S. Cl.
CPC .............. *A61F 2002/30777* (2013.01); *A61F 2002/30784* (2013.01); *A61F 2002/30825* (2013.01); *A61F 2002/30827* (2013.01); *A61F 2002/4475* (2013.01); *A61F 2220/0016* (2013.01)

(56) References Cited

U.S. PATENT DOCUMENTS

| | | | | |
|---|---|---|---|---|
| 2006/0293748 A1* | 12/2006 | Alexander | .............. | A61F 2/447 623/17.11 |
| 2010/0152857 A1* | 6/2010 | Freeman | ................. | A61F 2/447 623/17.16 |
| 2011/0166656 A1* | 7/2011 | Thalgott | ................ | A61F 2/4455 623/17.16 |
| 2012/0078370 A1* | 3/2012 | James | ..................... | A61F 2/442 623/17.16 |
| 2012/0158062 A1* | 6/2012 | Nunley | ................. | A61F 2/4455 606/249 |
| 2013/0090735 A1* | 4/2013 | Mermuys | .............. | A61F 2/4611 623/17.16 |
| 2013/0204374 A1* | 8/2013 | Milella, Jr. | ........... | A61F 2/4465 623/17.16 |

FOREIGN PATENT DOCUMENTS

| | | |
|---|---|---|
| KR | 10-2009-0015294 | 2/2009 |
| KR | 10-2012-0114283 | 10/2012 |

OTHER PUBLICATIONS

English translation of 10-2012-0114283.
English translation of JP2012-019919.
English translation of 10-2008-0113029.
English translation of 10-2009-0015294.

* cited by examiner

[Fig. 1]
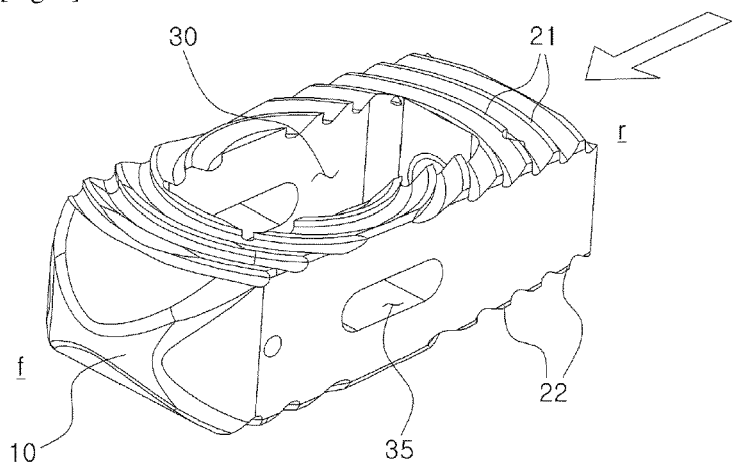
[Fig. 2]
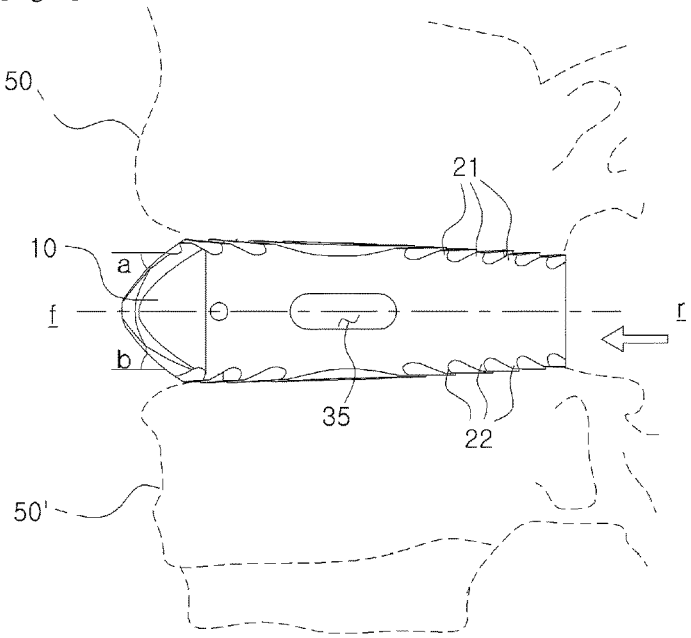
[Fig. 3]
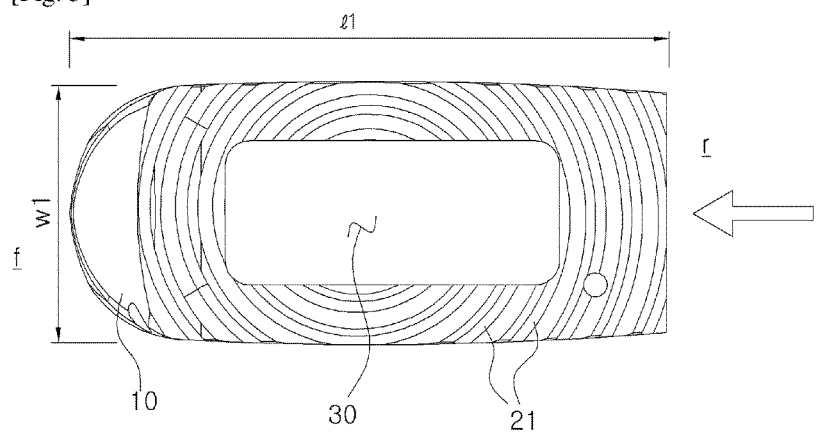

[Fig. 4]
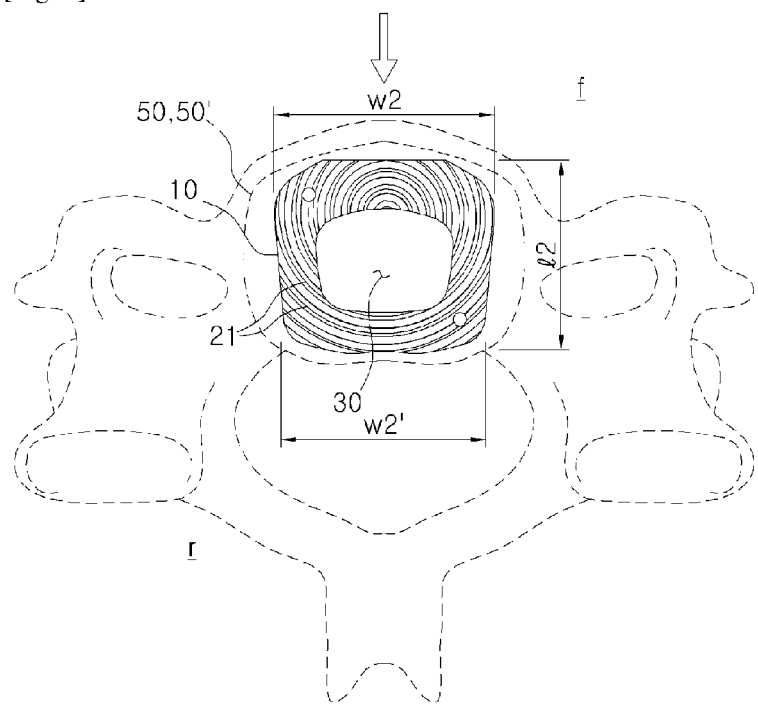
[Fig. 5]
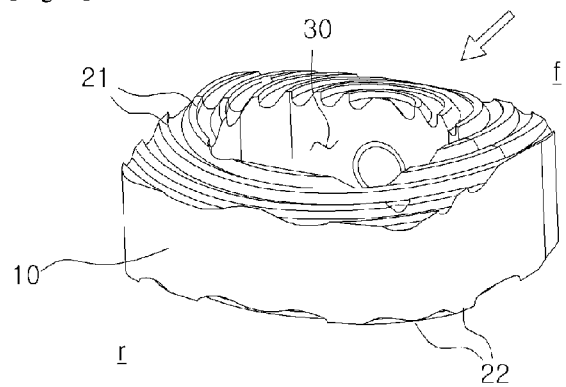
[Fig. 6]
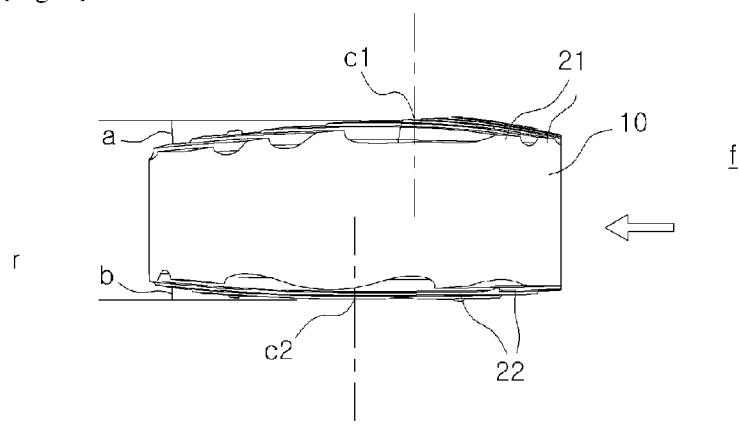

[Fig. 7]
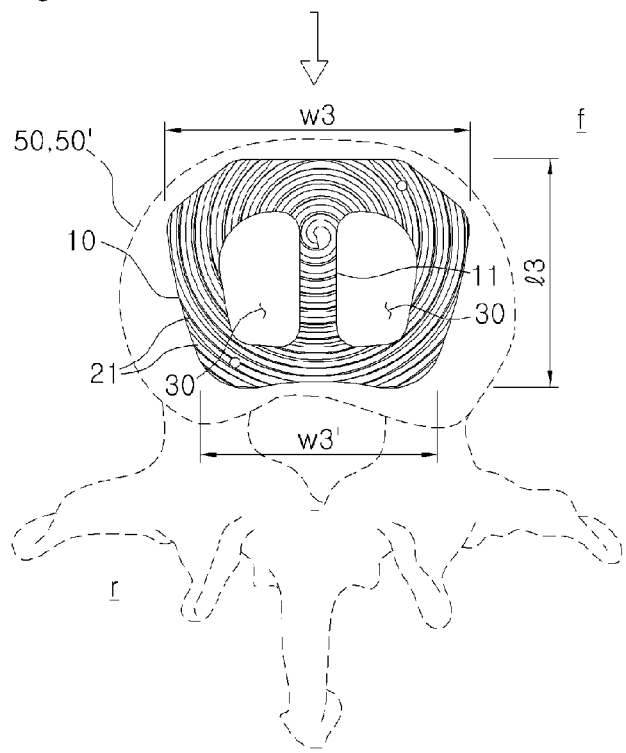
[Fig. 8]
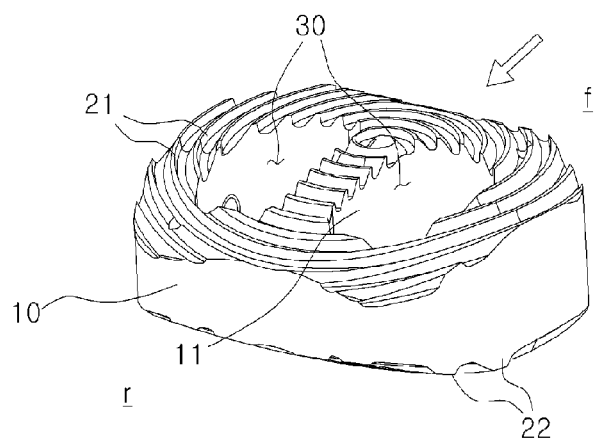
[Fig. 9]
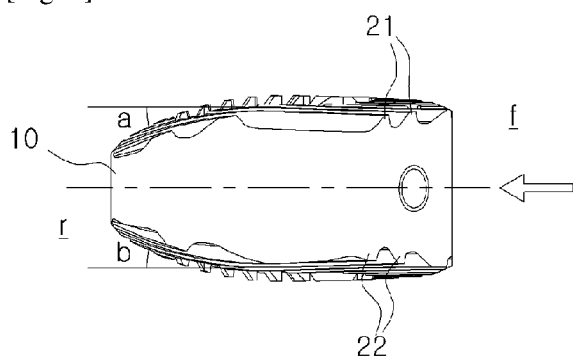

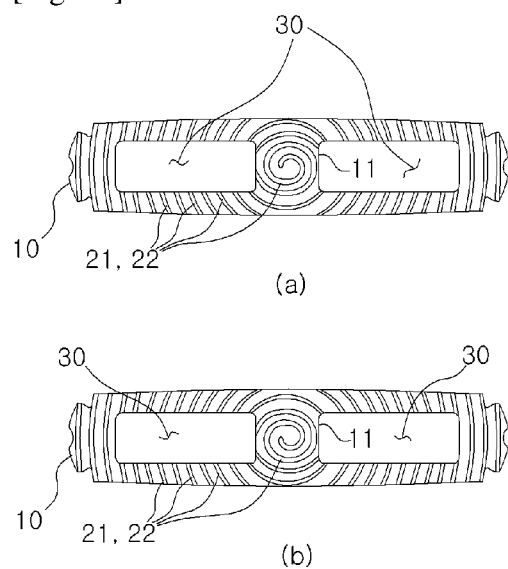
[Fig. 10]

CAGE ASSEMBLY FOR SPINE INTERBODY FUSION

TECHNICAL FIELD

The present invention relates to a cage assembly for spinal interbody fusion and, more particularly, to a cage assembly for spinal interbody fusion that supports a smooth surgical process of fusing two or more neighboring vertebral bodies constituting a spine.

BACKGROUND ART

Vertebral bodies include 32 to 35 vertebrae constructing a torso and intervertebral discs, and serve as a backbone of a human body that connects to cranial bones at an upper end of the human body to the pelvis at a lower end.

The vertebrae consist of 7 cervical vertebrae, 12 thoracic vertebrae, 5 lumbar vertebrae, 5 sacra, and 3 to 5 coccyges. For an adult, the 5 sacra fuse to form one sacral bone, and the 3 to 5 coccyges fuse to form one tailbone.

Spinal fusion has long been used as a method to treat severe spinal diseases. For example, some or all intervertebral discs need to be eliminated in a typical disc surgery.

This order is mainly performed on the cervical region and the lumbar region, but may also be performed on the thoracic region.

Cages which have been used for spinal interbody fusion come in various external shapes.

The upper and lower portions of a cage are formed in a shape of sawteeth arranged in a line in order to prevent displacement of the cage inserted into the vertebral body. However, it is not certain that the structure formed in the shape of sawteeth arranged in a line serves to prevent displacement of the cage.

Such conventional cages cannot stay fixed by itself, and thus need to be stably fixed using pedicle screws. Accordingly, it may take a considerable time to perform spinal interbody fusion. In addition, fusion of vertebral bodies may be retarded, or the cages may be displaced.

PRIOR ART LITERATURE

Patent Document

Korean Patent Application Publication No. 10-1992-0701023

DISCLOSURE

Technical Problem

An object of the present invention devised to solve the problem is to provide a cage assembly for spinal interbody fusion that supports a smooth surgical process of fusing two or more neighboring vertebral bodies constituting a spine.

Another object of the present invention is to provide a cage assembly for spinal interbody fusion that facilitates various reconstructive spinal surgeries and provide a fixation throe to a cage such that the cage is stably fixed between vertebral bodies to contribute to interbody fusion.

Technical Solution

The object of the present invention can be achieved by providing a cage assembly for spinal interbody fusion comprising: a main body inserted between a vertebral body of a spine from which a disc is removed and a neighboring vertebral body; a first screw part formed on an upper surface of the main body and formed in a spiral shape in a first direction pointing outward from a center thereof; a second screw part formed on a lower surface of the main body and formed in a spiral shape in a second direction pointing outward from a center thereof; and a hollow part formed to penetrate the upper surface and the lower surface of the main body, the hollow part being filled with an autogenous bone, a bone graft substitute or an allograft bone causing bones constituting the vertebral body and the neighboring vertebral body to fuse together.

Advantageous Effects

According to the present invention configured as above, a first screw part and a second screw part are formed on the upper surface and the lower surface of to main body respectively and spin in the same direction or opposite directions. Thereby, the main body inserted between neighboring vertebral bodies may be securely fixed.

In addition, as a hollow part into which a transplanted vertebra can be inserted is formed to penetrate the upper surface and the lower surface of the main body, the present invention may contribute to osteosis and mutual fusion of the neighboring vertebral bodies.

In addition, the present invention has a relatively simple structure and both lateral surfaces formed in a curved or streamlined shape, and therefore may facilitate the intervertebral body intromission procedure.

Moreover, the present invention is applicable to a variety of procedures such as Posterial Lumbar Interbody Fusion (PLIF), Transformational Lumbar Interbody Fusion (TLIF) Anterior Lumbar interbody Fusion (ALIF), Anterolateral Lumbar interbody Fusion (ALIF), Oblique-lateral Lumbar interbody Fusion (OLIF), Direct lateral Lumbar interbody Fusion (DLIF), or Anterior Cervical interbody Fusion (ACIF).

DESCRIPTION OF DRAWINGS

FIG. 1 is a perspective view illustrating an overall structure of a cage assembly for spinal interbody fusion according to an embodiment of the present invention.

FIG. 2 is a conceptual side view illustrating a cage assembly for spinal interbody fusion according to an embodiment of the present invention, which is inserted between a vertebral body and a neighboring vertebral body.

FIG. 3 is a conceptual plan view illustrating a cage assembly for spinal interbody fusion according to an embodiment of the present invention.

FIG. 4 is a conceptual plan view illustrating a cage assembly for spinal interbody fusion according to another embodiment of the present invention, which is inserted between a vertebral body and a neighboring vertebral body.

FIG. 5 is a perspective view illustrating a cage assembly for spinal interbody fusion according to another embodiment of the present invention.

FIG. 6 is a conceptual plan view illustrating a cage assembly for spinal interbody fusion according to an embodiment of the present invention.

FIG. 7 is a conceptual plan view illustrating a cage assembly for spinal interbody fusion according to another embodiment of the present invention, which is inserted between a vertebral body and a neighboring vertebral body.

FIG. 8 is a perspective view illustrating a cage assembly for spinal interbody fusion according to another embodiment of the present invention.

FIG. 9 is a conceptual side view illustrating a cage assembly for spinal interbody fusion according to an embodiment of the present invention.

FIG. 10 is a conceptual plan view illustrating a cage assembly for spinal interbody fusion according to yet another embodiment of the present invention.

BEST MODE

The advantages and features of the invention and methods to achieve the same will become apparent to those having ordinary skill in the art upon examination of the accompanying drawings and the following description of embodiments.

The present invention ma be embodied in many different forms and should not be construed as being limited to the embodiments set forth herein is not limited to the embodiments described herein, but may be embodied in other forms.

Rather, these embodiments are provided so that this disclosure will be thorough and complete, and will fully convey the concept of the invention to those skilled in the art.

In the drawings, the thicknesses of layers and regions are exaggerated for clarity.

The terms such as "upper end", "lower end", "upper surface", "lower surface", "upper portion", or "low portion", as used herein, are intended to distinguish between relative positions of elements.

For example, when an upper portion refers to the upper side of the drawings and a lower portion refers to the lower side of the drawings is called a lower portion for simplicity, the upper portion may be called a "lower portion" and the lower portion may be called an "upper portion" in reality without departing from the scope of the present invention.

Terms used in this specification are merely adopted to explain specific embodiments, and are not intended to limit the present invention.

As used herein, the singular forms "a", "an", and "the" are intended to include the plural forms as well, unless the context clearly indicates otherwise.

In this specification, a term "include" or "have" is intended to indicate that characteristics, figures, steps, operations, constituents, and components disclosed in the specification or combinations thereof exist. The term "include" or "have" should be understood as not pre-excluding possibility of existence or addition of one or more other characteristics, figures, steps, operations, constituents, components, or combinations thereof.

Unless otherwise defined, each technical or scientific term used herein has the same meaning as commonly understood by one of ordinary skill in the art to which the present invention belongs.

It should be understood that terms defined in a generally used dictionary have the same meaning as in a related technical context, and are not interpreted as an abnormal or excessively formal meaning unless clearly dictated in this specification.

Preferred embodiments of the present invention will now be described in detail with reference to the accompanying drawings.

FIG. 1 is a perspective view illustrating an overall structure of a cage assembly for spinal interbody fusion according to an embodiment of the present invention. FIG. 2 is a conceptual side view illustrating a cage assembly for spinal interbody fusion according to an embodiment of the present invention, which is inserted between a vertebral body and a neighboring vertebral body. FIG. 3 is a conceptual plan view illustrating a cage assembly for spinal interbody fusion according to an embodiment of the present invention.

For reference, the hollow arrows used in FIGS. 1 to 3 indicate the direction in which a main body 10 is inserted.

Reference symbols "f" and "r" used in FIGS. 1 to 9 indicate the "front side" and the "rear side", respectively.

As can be seen from the figures, the main body 10 according to the present invention includes first and second screw parts 21 and 22 and a hollow part 30.

The main body 10 is inserted between a vertebral body 50 and a neighboring vertebral body 50' of a spine from which a damaged disc has been removed. Thereby, the main body 10 occupies the space between the vertebral body 50 and the vertebral body 50' in place of the damaged disc.

The first screw part 21 is formed on the upper surface of the main body 10, and is arranged from the center outward in a spiral shape in a first direction. The second screw part 22 is formed on the lower surface of the main body 10, and is arranged from the center outward in a spiral shape in a second direction.

The hollow part 30 is a space which is formed by penetrating the upper surface and lower surface of the main body 10 and in which bones forming the vertebral body 50 and the neighboring vertebral body 50' fuse together.

The present invention may facilitate a procedure of fusing two neighboring vertebral bodies 50 and 50' or more vertebral bodies constituting the spine.

For the present invention, not only the embodiments described above but also embodiments described below are applicable.

The first direction of the first the screw party 21 may be the same as opposite to the second direction of the second screw part 22.

In this embodiment, the first direction is arranged to be opposite to the second direction. This is intended to prevent the main body 10 from being displaced from a position between the vertebral body 50 and the neighboring vertebral body 50 after the surgical procedure and to allow the cage assembly, namely the main body 10 to be self-fixed between the vertebral body 50 and the neighboring vertebral body 50'.

In other words, if the first direction is opposite to the second direction, the main body 10 will be self-fixed between the vertebral body 50 and the neighboring vertebral body 50' as the first and second screw parts 21 and 22 formed on the upper surface and lower surface of the main body 10 are inserted, into the vertebral bodies 50 and 50' when the spine makes a rotational movement.

For example, if the first direction is the clockwise direction, the first screw party 21 is formed clockwise, while the second screw part 22 is formed counterclockwise. Accordingly, the second direction becomes the counterclockwise direction.

If the first direction is the counterclockwise direction, the first screw part 21 is formed counterclockwise, while the second screw part 22 is formed clockwise. Accordingly, the second direction becomes the clockwise direction.

In other words, the first and second directions of the first and second screw parts 21 and 22 may be technical means adapted to allow the main body 10 to perform the function of self-fixation between the vertebral body 50 and the neighboring vertebral body 50' and to facilitate bone graft between the vertebral body 50 and the neighboring vertebral body 50'.

After the main body 10 is inserted between the vertebral body 50 and the neighboring vertebral body 50, the vertebral body 50 and the neighboring vertebral body 50' may make a fine rotational movement. Self-fixation refers to a fixation force produced by the first and second screw parts 21 and 22 of the main body 10 to prevent the fine rotational movement as the first and second screw parts 21 and 22 are inserted between the vertebral body 50 and the neighboring vertebral body 50'.

That is, bone graft is accelerated if a surgical procedure of minimizing or preventing a fine movement of the spine is performed after a fixation procedure such as an interbody intromission procedure using a cage for bone graft is conducted.

Accordingly, the self-fixation serves to accelerate bone graft of the vertebral body 50 and the neighboring vertebral body 50'. As shown in FIG. 2, the upper surface and the lower surface of the main body 10 are disposed to face surfaces of the vertebral body 50 and the neighboring vertebral body 50 facing each other, respectively. Thereby, the upper surface and the lower surface, prevent the main body 10 from being misaligned with the vertebral body 50 and the neighboring vertebral body 50'.

In addition, the upper surface and the lower surface of the main body 10 inserted between the vertebral body 50 and the neighboring vertebral body 50' may be arranged erect.

The front upper surface of the main body 10 is rounded downward, and the front lower surface of the main body 10 is rounded upward. Thereby, the front upper surface and the front lower surface are symmetrical. The main body 10 is inserted from the back side of a patient from whom a disc is removed, and is applicable to Posterial Lumbar Interbody Fusion (hereafter, PLIF).

The structure of the front upper surface and the front lower surface of the main body 10 is also commonly applicable not only to PLIF but also to Transforaminal Lumbar Interbody Fusion (TLIF), Anterolateral Lumbar Interbody Fusion (ALIF), Oblique-lateral Lumbar Interbody Fusion (OLIF) or Direct Lateral Lumbar Interbody Fusion (DLIF).

Herein, the inclination angle formed by the front upper surface and the front lower surface of the main body 10 which are symmetrical may be about 0°, 4° or 8° such that the angle corresponds to the lordotic angle.

In most spines of human bodies, the cervical region has a lordosis shape, the thoracic region has a kyphosis shape, and the lumbar region has a lordosis shape. Accordingly, the inclination angle formed by the front upper surface and the front lower surface of the main body 10 may be properly selected within the aforementioned range in designing the main body 10.

Accordingly, when PLIF is implemented, one main body 10 or a pair of main bodies 10 spaced from each other is inserted between the vertebral body 50 and the neighboring vertebral body 50' from the backside or transforaminal lumbar side.

Referring to FIG. 3, the hollow part 30 formed in the upper surface or the lower surface is adapted to have an area corresponding to 20 to 80% of the area of the upper surface or the lower surface. The area of the hollow part 30 may be within an optimum area range for maintaining structural strength after osteosis and bone graft between the vertebral body 50 and the neighboring vertebral body 50.

Preferably, at least one slot 35 communicating with the hollow part 30 is formed in opposite lateral surfaces of the main body 10 with respect to the insertion direction of the main body 10 in a penetrating manner.

The slot 35 is intended to confirm, in a radiological examination, if the bone graft has been successfully implemented and osseous tissues have been formed in the hollow part 30 of the main body 10 between the vertebral body 50 and the neighboring vertebral body 50 when a certain time passes after the spinal interbody fusion was performed.

As shown in FIG. 3, the opposite lateral surfaces of the main body 10 with respect to the insertion direction of the main body 10 are formed in a convex streamlined shape. The streamlined structure of the lateral surfaces facilitates insertion of the main body 10 between the vertebral body 50 and the neighboring vertebral body 50' from the backside of a patient from whom a disc has been removed.

The length l1 of the main body 10 in the insertion direction of the main body 10 may be greater than width w1 of the main body 10 in the direction perpendicular to the insertion direction of the main body 10. Thereby, the lateral surfaces of the main body 10 with respect to the insertion direction are adapted to have a convex and long bullet shape as a whole. Thereby, the main body 10 may be smoothly inserted between the vertebral body 50 and the neighboring vertebral body 50.

More preferably, the ratio of the width w1 and the length l1 is between 1:1.2 and 1:2 or may be changed and applied within a proper range.

The centers of the first screw part 21 and the second screw part 22 may be aligned with the center of the main body 10 or disposed in other positions such that the main body 10 is stably seated between the vertebral body 50 and the neighboring vertebral body 50' to support osteosis and bone graft between the vertebral body 50 and the neighboring vertebral body 50'.

The centers of the first and second screw parts 21 and 22 may be disposed outside the main body 10. Thereby, the first and second screw parts 21 and 22 of the main body 10 may be properly inserted between the vertebral body 50 and the neighboring vertebral body 50' according to the position of the main body 10 inserted between the vertebral body 50 and the neighboring vertebral body 50'. Thereby, a fixation force is produced to implement bone graft According to an embodiment of the present invention, the main body 10 of the cage assembly for spinal interbody fusion is inserted from the backside of a patient or between vertebral bodies of the patient. Specifically, a damaged disc between the vertebral body 50 and the neighboring vertebral body 50' is removed from the patient, and then one pair of main bodies 10 is inserted into the space from which the disc has been removed such that the vertebral body 50 and the neighboring vertebral body 50' fuse together.

The present invention is applicable not only to PLIF according to the embodiment illustrated in FIGS. 1 and 3 but also to Anterior Cervical Interbody Fusion (ACIF) according to the embodiment illustrated in FIGS. 4 to 6.

That is, when ACIF is implemented as shown in FIG. 4, the main body is inserted from the front side of the column of the patient from whom the disc has been removed The first screw part 21 formed on the upper surface of the main body 10 and the second screw part 22 formed on the lower surface of the main body 10 are arranged in the opposite directions. Thereby, the main body 10 is prevented from being displaced from the position between the vertebral body 50 and the neighboring vertebral body 50' and is fixed between the vertebral body 50 and the neighboring vertebral body 50' after the surgical procedure.

The first screw part 21 and the second screw part 22 may be formed in the opposite directions as described above or be formed in the same direction.

The width w2 of the front side of the main body 10 is greater than the width w2' of the rear side of the main body 10 with respect to the insertion direction of the main body 10. This structure is a technical means to facilitate insertion of the main body 10 from the front side of the column of the patient.

Preferably, the center of the hollow part 30 is aligned with the centers of the upper surface and lower surface of the main body 10 such that the main body 10 is stably seated between the vertebral body 50 and the neighboring vertebral body 50'.

In other words, the upper surface or lower surface of the main body 10 and the hollow part 30 are adapted to be gradually narrowed as they extend from the rear side to the front side with respect to the insertion direction of the main body 10.

As shown in FIG. 4, the upper surface and lower surface of the main body 10 face surfaces of the vertebral body 50 and the neighboring, vertebral body 50' facing each other, respectively. The hollow part 30 formed in the upper surface or the lower surface is adapted to occupy an area corresponding to 20 to 80% of the area of the upper surface or the lower surface of the main body 10.

The area of the hollow part 30 may be within an optimum area range for maintaining structural strength after osteosis and bone graft between the vertebral body 50 and the neighboring vertebral body 50'.

The length l2 of insertion of the main body 10 may be less than or equal to the width w2 of the rear side of the main body 10. The ratio of the length l2 and the width w2 may be properly changed and applied within a range between about 1:1.2 and about 1:2.

Such ratio, width and length are provided to the structure because the surfaces of the vertebral body 50 and the neighboring vertebral body 50' facing each other approximately correspond to the shape of the upper surface and lower surface of the main body 10 which is formed such that the front side width w2 is greater than the rear side width w2'. The ratio, width and length specified above are intended to support the vertebral body 50 and the neighboring vertebral body 50' with structural strength maintained over a relatively wide area and support osteosis which cause the vertebral body 50 and the neighboring vertebral body 50' to fuse together.

As shown in FIGS. 5 and 6, the front upper surface of the main body 10 is rounded downward at a first angle (a), and the rear lower surface of the main body 10 is rounded upward at a second angle (b) which is less than or equal to the first angle (a). Thereby, the upper surface and the lower surface are formed in a streamlined shape.

Usually, the first angle (a) is set to be greater than the second angle (b). Preferably, the first angle (a) is set to be about three times the second angle (b). Setting the second angle (b) to be less than the first angle (a) is intended to maintain natural arrangement of the vertebral body 50 and the neighboring vertebral body 50' according to structural properties of the cervical region of cervical vertebrae which form the shape of letter C shape, i.e., a lordotic shape as a whole when viewed from a lateral side.

That is, in contrast with the main body 10 for PLIF or ALIF, which will be described later, the front upper surface and front lower surface of the main body 10 of this embodiment are formed to be asymmetrical in consideration of the lordotic angle of the lower portion of the lumber vertebra and anatomical features of the vertebral body 50 and the neighboring vertebral body 50'.

The structure of the upper and lower surfaces of the main body 10 formed in this manner is applicable not only to PLIF but also to Transforaminal Lumbar Interbody Fusion (TLIF), Anterolateral Lumbar Interbody Fusion (ALIF), Oblique-lateral Lumbar Interbody Fusion (OLIF), or Direct lateral Lumbar Interbody Fusion (DLIF).

While FIGS. 4 and 5 illustrate that the center of the first screw part 21 or the second screw part 22 is misaligned with the center of the upper surface or lower surface of the main body 10 according to another embodiment of the cage assembly for spinal interbody fusion, the present invention is not limited thereto.

Specifically, the center of the first screw part 21 or the second screw part 22 may be aligned with the center of the upper surface or lower surface of the main body 10, or may be positioned at a point spaced from the front edge of the upper surface or lower surface by one-third of the length of the main body 10 in the insertion direction of the main body 10. Alternatively, the center of the first screw part 21 or the second screw part 22 may be spaced from the rear side of the upper or lower surface of the main body 10 or disposed inside or outside the main body 10.

According to another embodiment, the main body 10 of the cage assembly is inserted from the front side of the column of a patient. Specifically, after a damaged disc is removed from a space between the vertebral body 50 and the neighboring vertebral body 50', and then the main body 10 is inserted into the space. Thereafter, a bone fragment (not shown), namely an autogenous bone chip collected from the pelvis of the patient, an artificially fabricated bone graft substitute or an allograft bone is inserted into the hollow part 30. Then, the vertebral body 50 and the neighboring vertebral body 50' fuse together using the bone fragment as a medium.

This embodiment is applicable to PLIF according to the embodiment of FIGS. 1 to 3, ACIF as illustrated, in FIGS. 4 to 6, and Anterior Lumbar Interbody Fusion (ALIF) as illustrated in FIGS. 7 to 9. The embodiment is also applicable to Anterolateral Lumbar Interbody Fusion (ALIF), Oblique-lateral Lumbar Interbody Fusion (OLIF), or Direct lateral Lumbar interbody Fusion (DLIF).

That is, the main body 10 is inserted from the front, the abdomen or the retroperitoneum of a patient from whom a disc has been removed in implementing ALIF as illustrated in FIG. 7.

The width w3 of the front side of the main body 10 is greater than the width w3' of the rear side of the main body 10 with respect to the insertion direction of the main body 10. This structure is a technical means to facilitate insertion of the main body 10 from the front side of the lumbar region of the patient.

Preferably, the center of the hollow part 30 is aligned with the centers of the upper surface and lower surface of the main body 10 such that the main body 10 is stably seated between the vertebral body 50 and the neighboring vertebral body 50'.

In other words, the upper surface or lower surface of the main body 10 and the hollow part 30 are adapted to be gradually narrowed as they extend from the front side to the rear side with respect to the insertion direction of the main body 10.

As shown in FIG. 7, the upper surface and lower surface of the main body 10 face surfaces of the vertebral body 50 and the neighboring vertebral body 50 facing each other, respectively. The hollow part 30 formed in the upper surface or the lower surface is adapted to occupy an area corresponding to 20 to 80% of the area of the upper surface or the lower surface of the main body 10.

The area of the hollow party 30 may be within an optimum area range for maintaining structural strength after osteosis and bone graft between the vertebral body 50 and the neighboring vertebral body 50'.

According to an embodiment, a partition part 11 may be provided to the main body 10 to divide the hollow part 30 into a plurality of parts arranged in the direction of insertion of the main body 10.

The partition part 11 is intended to contribute to structural stability of the main body to and stably fix the centers of the first and second screw parts 21 and 22 between the vertebral body 50 and the neighboring vertebral body 50.

The length l3 of the main body 10 in the insertion direction of the main body 10 may be less than the width w3 of the front side of the main body 10. The ratio of the length l3 and the width w3 may be properly changed and applied within a range between about 1:1.2 and about 1:2.

Such ratio, width and length are provided to the structure because the surfaces of the vertebral body 50 and the neighboring vertebral body 50' facing each other approximately correspond to the shape of the upper surface and lower surface of the main body 10 which is formed such that the front side width w2 is greater than the rear side width w2'. The ratio, width and length specified above are intended to support the vertebral body 50 and the neighboring vertebral body 50' with structural strength maintained over a relatively wide area and support osteosis that causes the vertebral body 50 and the neighboring vertebral body 50' to fuse.

The front upper surface of the main body 10 is rounded downward, and the front lower surface of the main body 10 is rounded upward. Thereby, the front upper surface and the front lower surface are symmetrical and formed in a convex shape as a whole. Accordingly, when ALIF is conducted, the main body 10 may be smoothly inserted between the vertebral body 50 and the neighboring vertebral body 50'.

While FIGS. 7 to 9 illustrate that the center of the first screw part 21 or the second screw part 22 is misaligned with the center of the upper surface or lower surface of the main body 10 according to another embodiment of the cage assembly for spinal interbody fusion, the present invention is not limited thereto.

Specifically, the center of the first screw part 21 or the second screw part 22 may be aligned with the center of the upper surface or lower surface of the main body 10, or may be positioned at a point spaced from the rear edge of the upper surface or lower surface by one-third of the length of the main body 10 in the insertion direction of the main body 10. Alternatively, the center of the first screw part 21 or the second screw part 22 may be spaced from the rear side of the upper or lower surface of the main body 10 or disposed inside or outside the main body 10.

According to another embodiment, the main body 10 of the cage assembly is inserted from the front side of the column of a patient. Specifically, after a damaged disc is removed from a space between the vertebral body 50 and the neighboring vertebral body 50', the main body 10 is inserted into the space. Thereafter, a bone fragment (not shown), namely an autogenous bone chip collected from the pelvis of the patient, an artificially fabricated bone graft substitute or an allograft bone is inserted into the hollow part 30. Then, the vertebral body 50 and the neighboring vertebral body 50 fuse together using the bone fragment as a medium.

As can be seen from the descriptions above, the present invention is basically intended to provide a cage assembly for spinal interbody fusion which facilitates a surgical procedure of fusing two or more vertebral bodies or a region from which at part of neighboring vertebral bodies constituting a spine has been removed.

It will be apparent to those skilled in the art that a cage assembly for spinal interbody fusion according to various embodiments of the present invention is applicable not only to PLIF, ACIF and ALIF as described above and also to Transforaminal Lumbar Interbody Fusion (TLIF), Anterolateral Lumbar Interbody Fusion (ALIF) or Oblique-lateral Lumbar Interbody Fusion (OLIF) within the technical scope of the present invention.

According to an embodiment, a plurality of hollow parts 30 may be formed in the longitudinal direction of the main body 10, and a first screw part 21 and a second screw part 22 may be formed around each hollow part 13. In addition, the front and rear upper surfaces of the main body 10 may be rounded downward and the front and rear lower surface of the main body 10 may be rounded upward such that the upper surface and the lower surface are symmetrical. This embodiment it is widely applicable, for example, to Direct Lateral Lumbar Interbody Fusion (DLIF).

Herein, the main body 10 may further include a partition part 11 for dividing the hollow part 30 into a plurality of hollow parts as shown in the figure.

Various changes and modifications can be made to this embodiment. For example, the centers of the first screw part 21 and the second screw part 22 may be disposed on the partition part 11 as shown in FIGS. 10(a) and 10(b). Alternatively, although not shown in the figures, the centers of the first screw part 21 and the second screw part 22 may be aligned with the hollow part 30 or disposed inside or outside the hollow part 30 or inside or outside the main body 10.

The invention claimed is:

1. A cage assembly for spinal interbody fusion comprising:
    a main body configured to be inserted between a vertebral body of a spine from which a disc is removed and a neighboring vertebral body;
    a first screw part formed on an upper surface of the main body and formed in a spiral shape in a first direction pointing outward from a center thereof;
    a second screw part formed on a lower surface of the main body and formed in a spiral shape in a second direction pointing outward from a center thereof, the second direction being opposite to the first direction; and
    a hollow part formed to extend between the upper surface and the lower surface of the main body, the hollow part allowing bones constituting the vertebral body and the neighboring vertebral body to fuse together, wherein one of the first screw part and the second screw part are formed in a clockwise spiral, and the other of the first screw part and the second screw part are formed in a counterclockwise spiral.

2. The cage assembly according to claim 1, wherein a front upper surface of the main body is rounded downward and a front lower surface of the main body is rounded upward, the front upper surface and the front lower surface being symmetrical,
    wherein the main body is configured to be inserted between a vertebral body of a patient from whom the disc is removed and a neighboring vertebral body.

3. The cage assembly according to claim 1, wherein opposite lateral surfaces of the main body with respect to a direction of insertion of the main body are convexly streamlined.

4. The cage assembly according to claim 1, wherein a length of the main body in a direction of insertion of the main body is greater than a width of the main body in a direction perpendicular to the direction of insertion of the main body.

5. The cage assembly according to claim 1, wherein the centers of the first screw part and the second screw part are aligned with a center of the main body or disposed at different positions on the upper surface and the lower surface of the main body, respectively.

6. The cage assembly according to claim 1, wherein the centers of the first screw part and the second screw part are disposed inside or outside the main body.

7. The cage assembly according to claim 1, wherein a rear upper surface of the main body is rounded downward at a first angle and a rear lower surface of the main body is rounded upward such that the main body being streamlined,
wherein the main body is configured to be inserted from a front side of a column of a patient from whom the disc is removed.

8. The cage assembly according to claim 7, wherein the upper surface of the main body is convex upward, and the lower surface of the main body is convex downward.

9. The cage assembly according to claim 1, wherein a rear upper surface of the main body is rounded downward, and a rear lower surface of the main body is rounded upward, the rear upper surface and the rear lower surface being symmetrical,
wherein the main body is configured to be inserted from an abdomen or a retroperitoneum of a patient from whom the disc is removed.

10. The cage assembly according to claim 1, wherein a width of a front side of the main body is greater than a width of a rear side of the main body with respect to a direction of insertion of the main body,
wherein a center of the hollow part is aligned with a center of the upper surface or the lower surface.

11. The cage assembly according to claim 10, wherein a length of the main body in the direction of insertion of the main body is less than the width of the front side of the main body.

12. The cage assembly according to claim 1, wherein a width of a front side of the main body is greater than a width of a rear side of the main body with respect to a direction of insertion of the main body,
wherein a center of the hollow part is aligned with a center of the upper surface or the lower surface,
wherein the center of the first screw part or the second screw part coincides with the upper surface or the lower surface or is disposed inside or outside the main body.

13. The cage assembly according to claim 1, wherein a width of a front side of the main body is greater than a width of a rear side of the main body with respect to a direction of insertion of the main body,
wherein a center of the hollow part is aligned with a center of the upper surface or the lower surface,
wherein the center of the first screw part or the second screw part is formed at a point spaced from a front edge of the upper surface or the lower surface by one-third of a length of the main body in the direction of insertion of the main body, or disposed inside or outside the main body.

14. The cage assembly according to claim 1, wherein a width of a rear side of the main body is greater than a width of a front side of the main body with respect to a direction of insertion of the main body,
wherein a center of the hollow part is aligned with a center of the upper surface or the lower surface,
wherein the center of the first screw part or the second screw part is spaced from a rear side of the upper surface or the lower surface or disposed inside or outside the main body.

15. The cage assembly according to claim 1, further comprising:
a partition part providing to the main body to divide the hollow part along a direction of insertion of the main body,
wherein the centers of the first screw part and the second screw part are positioned on the partition part.

16. The cage assembly according to claim 1, wherein front and rear upper surfaces of the main body are rounded downward, and front and rear lower surfaces of the main body are rounded upward, the front and rear upper surfaces of the main body being symmetrical to the front and rear lower surfaces of the main body,
wherein the hollow part comprises a plurality of hollow parts arranged in a longitudinal direction of the main body, the first screw part and the second screw part being formed around each of the hollow parts,
wherein the centers of the first screw part and the second screw part are aligned with centers of the hollow parts, disposed inside or outside the hollow parts, or disposed inside or outside the main body.

17. The cage assembly according to claim 16, further comprising:
a partition part providing to the main body to divide the hollow part,
wherein the centers of the first screw part and the second screw part are positioned on the partition part.

* * * * *